United States Patent [19]

Bezwada et al.

[11] Patent Number: 5,464,929
[45] Date of Patent: Nov. 7, 1995

[54] ABSORBABLE POLYOXAESTERS

[75] Inventors: Rao S. Bezwada, Whitehouse Station; Dennis D. Jamiolkowski, Long Valley, both of N.J.

[73] Assignee: Ethicon, Inc., Somerville, N.J.

[21] Appl. No.: 399,308

[22] Filed: Mar. 6, 1995

[51] Int. Cl.$^6$ .................................................. C08G 63/66
[52] U.S. Cl. .................... 528/361; 528/272; 528/301; 424/426; 424/430; 424/433; 424/444; 424/446; 424/448; 424/486
[58] Field of Search .................... 528/272, 301, 528/361; 424/426, 430, 433, 444, 446, 448, 486

[56] References Cited

U.S. PATENT DOCUMENTS

| | | | |
|---|---|---|---|
| 4,440,922 | 4/1984 | Barbee et al. | 528/194 |
| 4,510,295 | 4/1985 | Bezwada et al. | 525/437 |
| 4,546,152 | 10/1985 | Koelmel et al. | 529/437 |
| 4,552,948 | 11/1985 | Barbee et al. | 528/194 |
| 4,689,424 | 8/1987 | Shalaby et al. | 560/61 |
| 4,730,069 | 3/1988 | Kolar et al. | 556/137 |
| 4,963,641 | 10/1990 | Davis | 528/190 |
| 5,349,028 | 9/1994 | Takahashi et al. | 525/440 |

*Primary Examiner*—Samuel A. Acquah

[57] ABSTRACT

The present invention describes a new aliphatic polyoxaesters that is bioabsorbable and may be used to produce surgical devices such as sutures, sutures with attached needles, molded devices, and the like. The invention also contemplates a process for producing these polyesters. The aliphatic polyoxaesters of the present invention have a first divalent repeating unit of formula I:

$$[O-C(O)-C(R_1)(R_2)-O-(R_3)-O-C(R_1)(R_2)-C(O)-] \qquad I$$

and a second repeating unit selected from the group of formulas consisting of:

$$+O-R_4\tfrac{}{A}, \qquad II$$

$$+O-R_5-C(O)\tfrac{}{B}, \qquad III$$

and $$([-O-R_5-C(O)]_p-O-)_L G \qquad XI$$

and combinations thereof.

22 Claims, No Drawings

ABSORBABLE POLYOXAESTERS

FIELD OF THE INVENTION

The present invention relates to a bioabsorbable polymeric material and more particularly to absorbable surgical products made from such polymers.

BACKGROUND OF THE INVENTION

Since Carothers early work in the 1920s and 1930s, aromatic polyesters particularly poly(ethylene terephthalate) have become the most commercial important polyesters. The usefulness of these polymers is intimately linked to the stiffening action of the pphenylene group in the polymer chain. The presence of the p-phenylene group in the backbone of the polymer chain leads to high melting points and good mechanical properties especially for fibers, films and some molded products. In fact poly(ethylene terephthalate) has become the polymer of choice for many common consumer products, such as one and two liter soft drink containers.

Several related polyester resins have been described in U.S. Pat. Nos. 4,440,922, 4,552,948 and 4,963,641 which seek to improve upon the properties of poly(ethylene terephthalate) by replacing terephthalic acid with other related dicarboxylic acids which contain phenylene groups. These polymers are generally designed to reduce the gas permeability of aromatic polyesters.

Other aromatic polyesters have also been developed for specialty applications such as radiation stable bioabsorbable materials. U.S. Pat. Nos. 4,510,295, 4,546,152 and 4,689, 424 describe radiation sterilizable aromatic polyesters which can be used to make sutures and the like. These polymers like, poly(ethylene terephthalate), have phenylene groups in the backbone of the polymers.

However, less research has been reported on aliphatic polyesters. After Carothers initial work on polyesters, aliphatic polyesters were generally ignored because it was believed that these materials had low melting points and high solubilities. The only aliphatic polyesters that have been extensively studied are polylactones such as polylactide, polyglycolide, poly(p-dioxanone) and polycaprolactone. These aliphatic polylactones have been used primarily for bioabsorbable surgical sutures and surgical devices such as staples. Although polylactones have proven to be useful in many applications they do not meet all the needs of the medical community. For example films of polylactones do not readily transmit water vapor, therefore, are not ideally suited for use as bandages where the transmission of water vapor would be desired.

Only recently has there been renewed interest in nonlactone aliphatic polyesters. U.S. Pat. No. 5,349,028 describes the formation of very simple aliphatic polyesters based on the reaction of a diol with a dicarboxylic acid to form a prepolymer chain that are then coupled together. These polyesters are being promoted for 25 use in fibers and molded articles because these polyesters are biodegradable after they are buried such as in a landfill. However, these materials are not disclosed as being suitable for use in surgical devices.

Thus it is an object of the present invention to provide a new class of aliphatic polyesters that are bioabsorbable and may be used in surgical devices such as sutures, molded devices, drug delivery matrices, coatings, lubricants and the like.

SUMMARY OF THE INVENTION

We have discovered a new class of synthetic polymeric materials that are bioabsorbable and may be used to produce surgical devices such as sutures, sutures with attached needles, molded devices, drug delivery matrices, coatings, lubricants and the like. The invention also contemplates a process for producing the bioabsorbable polymers and copolymers. The aliphatic polyoxaesters of the present invention are polyesters comprising a first divalent repeating unit of formula I:

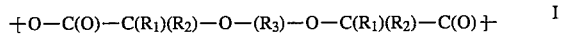

and a second repeating unit selected from the group of formulas consisting of:

and combinations thereof, wherein $R_1$ and $R_2$ are independently hydrogen or an alkyl group containing 1 to 8 carbon atoms; $R_3$ is an alkylene unit containing from 2 to 12 carbon atoms or is an oxyalkylene group of the following formula:

$$-[(CH_2)_C-O-]_D-(CH_2)_E- \qquad IV$$

wherein C is an integer in the range of from 2 to about 5, D is an integer in the range of from about 1 to about 12, and E is an integer in the range of from about 2 to about 5; $R_4$ is an alkylene unit containing from 2 to 8 carbon atoms; A is an integer in the range of from 1 to 1,000; $R_5$ is selected from the group consisting of $-C(R_6)(R_7)-$, $-(CH_2)_3-O-$, $-CH_2-CH_2-O-CH_2-$, $-CR_8H-CH_2-$, $-(CH_2)_4-$, $-(CH_2)_F-O-C(O)-$ and $-(CH_2)_F-C(O)-CH_2-$; $R_6$ and $R_7$ are independently hydrogen or an alkyl containing from 1 to 8 carbon atoms; $R_8$ is hydrogen or methyl; F is an integer in the range of from 2 to 6; B is an integer in the range of from 1 to n such that the molecular weight of formula III is less than about 40,000; P is an integer in the range of from 1 to m such that the molecular weight of formula XI is less than about 40,000; G represents the residue minus from 1 to L hydrogen atoms from the hydroxyl group of an alcohol previously containing from 2 to 12 hydroxyl groups; and L is an integer from about 1 to about 12.

DETAILED DESCRIPTION OF THE INVENTION

The aliphatic polyoxaesters of the present invention are the reaction product of an aliphatic polyoxycarboxylic acid and at least one of the following compounds: a diol (or polydiol), a lactone (or lactone oligomer), a coupling agent or combination thereof.

Suitable aliphatic alpha-oxycarboxylic acids for use in the present invention generally have the following formula:

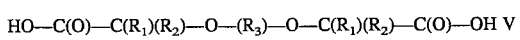

wherein $R_1$ and $R_2$ are independently selected from the group consisting of hydrogen or an alkyl group containing from 1 to 8 carbon atoms and R3 is an alkylene containing from 2 to 12 carbon atoms or is an oxyalkylene group of the following formula:

$$-[(CH_2)_C-O-]_D-(CH_2)_E- \qquad IV$$

wherein C is an integer in the range of from about 2 to about 5, D is an integer in the range of from about 0 to about 12, and E is an integer in the range of from about 2 to about 5. These aliphatic alpha-hydroxycarboxylic acids may be formed by reacting a diol or polydiol with an alpha-halocarboxylic acid such bromoacetic acid or chloroacetic acid under suitable conditions.

Suitable diols or polydiols for use in the present invention are diol or diol repeating units with up to 8 carbon atoms having the formulas:

$$H[-(O-R_4-)_A]OH, \text{ or} \qquad VI$$

wherein $R_4$ is an alkylene unit containing from 2 to 8 methylene units; A is an integer in the range of from 1 to about 1000. Examples of suitable diols include diols selected from the group consisting of 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol and combinations thereof. Examples of preferred polydiols include polydiols selected from the group consisting of polyethylene glycol ($H[-O-CH_2-CH_2-]_AOH$) and polypropylene glycol ($H[-O-CH_2-CH(CH_3)-]_AOH$).

The polymer produced by reacting the aliphatic dioxycarboxylic acid with the diols discussed above should provide a polymer generally having the formula:

$$[-O-C(O)-C(R_1)(R_2)-O-(R_3)-O-C(R_1)(R_2)-C(O)-(O-R_4)_A-]_N \qquad VII$$

wherein $R_1$, $R_2$, $R_3$, $R_4$ and A are as described above; and N is an integer in the range of from about 1 to about 10,000 and preferably is in the range of from about 10 to about 1,000 and most preferably in the range of from about 50 to about 200.

Suitable lactone monomers that may be used in the present invention generally have the formula:

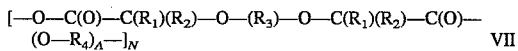

$$\left[-O-R_5-C(O)-\right], \qquad VIII$$

These lactone monomers may be polymerized to provide polymers of the following general structures:

$$H[-O-R_5-C(O)-]_BOH \qquad IX$$

$$(H[-O-R_5-C(O)]_P-O-)_LG \qquad X$$

wherein $R_5$ is selected from the group consisting of $-C(R_6)(R_7)-$, $-(CH_2)_3-O-$, $-CH_2-CH_2-O-CH_2-$, $-CR_8H-CH_2-$, $-(CH_2)_4-$, $-(CH_2)_F-O-C(O)-$ and $-(CH_2)_F-C(O)-CH_2-$; $R_6$ and $R_7$ are independently hydrogen or an alkyl containing from 1 to 8 carbon atoms; $R_8$ is hydrogen or methyl; F is an integer of from about 2 to 6; B is an integer in the range of from 1 to n such that the molecular weight of formula IX is less than about 40,000; P is an integer in the range of from 1 to m such that the molecular weight of formula X is less than about 40,000; G represents the residue minus from 1 to L hydrogen atoms from the hydroxyl groups of an alcohol previously containing from 2 to 12 hydroxyl groups; and L is an integer from about 1 to about 12. Preferably G will be the residue of a dihydroxy alcohol minus both hydroxyl groups and the molecular weights of formulas IX and X will be less than about 40,000. Suitable lactone-derived repeating units may be generated from the following monomers include but are not limited to lactone monomers selected from the group consisting of glycolide, d-lactide, l-lactide, meso-lactide, ε-caprolactone, p-dioxanone, trimethylene carbonate, 1,4-dioxepan-2-one, 1,5-dioxepan-2-one and combinations thereof.

The polymer formed by reacting the above described diol (or polydiol) VI and the aliphatic polyoxycarboxylic acid V may also be copolymerized in a condensation polymerization with the lactone polymers IX described above to form a polymer generally of the formula: $[(-C(O)-C(R_1)(R_2)-O-R_3-O-C(R_1)(R_2)-C(O)-(O-R_4)_A-O)_S(C(O)-R_5-O)_B]_W$ +tm XII or

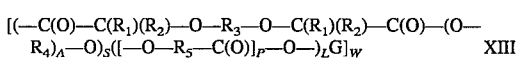

$$[(-C(O)-C(R_1)(R_2)-O-R_3-O-C(R_1)(R_2)-C(O)-(O-R_4)_A-O)_S([-O-R_5-C(O)]_P-O-)_LG]_W \qquad XIII$$

wherein S and W are independently integers in the range of from about 1 to about 1,000. These polymers may be made in the form of random copolymers or block copolymers. To the diols, aliphatic polyoxycarboxylic acids and lactone monomers described above there may be added a coupling agent selected from the group consisting of trifunctional or tetrafunctional polyols, oxycarboxylic acids, and polybasic carboxylic acids (or acid anhydrides thereof). The addition of the coupling agents causes the branching of long chains, which can impart desirable properties in the molten state to the polyester prepolymer. Examples of suitable polyfunctional coupling agents include trimethylol propane, glycerin, pentaerythritol, malic acid, citric acid, tartaric acid, trimesic acid, propane tricarboxylic acid, cyclopentane tetracarboxylic anhydride and combinations thereof.

The amount of coupling agent to be added before gelation occurs is a function of the type of coupling agent used and the polymerization conditions of the polyoxaester or molecular weight of the prepolymer to which it is added. Generally in the range of from about 0.1 to about 10 mole percent of a trifunctional or a tetrafunctional coupling agent may be added based on the moles of aliphatic polyoxaester polymers present or anticipated from the synthesis.

The polymerization of the aliphatic polyoxaester is preferably performed under melt polycondensation conditions in the presence of an organometallic catalyst at elevated temperatures. The organometallic catalyst is preferably a tin-based catalyst e.g. stannous octoate. The catalyst will preferably be present in the mixture at a mole ratio of diol, aliphatic polyoxycarboxylic acid and optionally lactone monomer to catalyst will be in the range of from about 15,000 to 80,000/1. The reaction is preferably performed at a temperature no less than about 120° C. under reduced pressure. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and the glass transition temperature and softening temperature of the polymer. The preferred reaction conditions of temperature, time and pressure can be readily determined by assessing these and other factors.

Generally, the reaction mixture will be maintained at about 220° C. The polymerization reaction can be allowed to proceed at this temperature until the desired molecular weight and percent conversion is achieved for the copolymer, which will typically take about 15 minutes to 24 hours. Increasing the reaction temperature generally decreases the reaction time needed to achieve a particular molecular weight.

In another embodiment, copolymers of aliphatic polyoxaester can be prepared by forming an aliphatic polyoxaester prepolymer polymerized under melt polycondensation conditions, then adding at least one lactone monomer or lactone prepolymer. The mixture would then be subjected to the desired conditions of temperature and time to copolymerize the prepolymer with the lactone monomers.

The molecular weight of the prepolymer as well as its composition can be varied depending on the desired characteristic which the prepolymer is to impart to the copolymer. However, it is preferred that the aliphatic polyoxaester prepolymers from which the copolymer is prepared have a molecular weight that provides an inherent viscosity between about 0.2 to about 2.0 deciliters per gram (dl/g) as measured in a 0.1 g/dl solution of hexafluoroisopropanol at 25° C. Those skilled in the art will recognize that the aliphatic polyoxaester prepolymers described herein can also be made from mixtures of more than one diol or dioxycarboxylic acid.

One of the beneficial properties of the aliphatic polyoxaester made by the process of this invention is that the ester linkages are hydrolytically unstable, and therefore the polymer is bioabsorbable because it readily breaks down into small segments when exposed to moist bodily tissue. In this regard, while it is envisioned that co-reactants could be incorporated into the reaction mixture of the aliphatic dioxycarboxylic acid and the diol for the formation of the aliphatic polyoxaester prepolymer, it is preferable that the reaction mixture does not contain a concentration of any co-reactant which would render the subsequently prepared polymer nonabsorbable. Preferably, the reaction mixture is substantially free of any such co-reactants if the resulting polymer is rendered nonabsorbable.

The polymers of this invention can be melt processed by numerous methods to prepare a vast array of useful devices. These polymers can be injection or compression molded to make implantable medical and surgical devices, especially wound closure devices. The preferred wound closure devices are surgical clips, staples and sutures.

Alternatively, the aliphatic polyoxaesters can be extruded to prepare fibers. The filaments thus produced may be fabricated into sutures or ligatures, attached to surgical needles, packaged, and sterilized by known techniques. The polymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for typing up and supporting damaged surface abrasions, particularly major abrasions, or areas where the skin and underlying tissues are damaged or surgically removed.

Additionally, the polymers can be molded to form films which, when sterilized, are useful as adhesion prevention barriers. Another alternative processing technique for the polymers of this invention includes solvent casting, particularly for those applications where a drug delivery matrix is desired.

In more detail, the surgical and medical uses of the filaments, films, and molded articles of the present invention include, but are not necessarily limited to:

Knitted products, woven or non-woven, and molded products including:
a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. suture knot clip
j. orthopedic pins, clamps, screws, and plates
k. clips (e.g., for vena cava)
l. staples
m. hooks, buttons, and snaps
n. bone substitutes (e.g., mandible prosthesis)
o. intrauterine devices (e.g., spermicidal devices)
p. draining or testing tubes or capillaries
q. surgical instruments
r. vascular implants or supports
s. vertebral discs
t. extracorporeal tubing for kidney and heart-lung machines
u. artificial skin and others.

In another embodiment, the aliphatic polyoxaester is used to coat a surface of a surgical article to enhance the lubricity of the coated surface. The polymer may be applied as a coating using conventional techniques. For example, the polymer may be solubilized in a dilute solution of a volatile organic solvent, e.g. acetone, methanol, ethyl acetate or toluene, and then the article can be immersed in the solution to coat its surface. Once the surface is coated, the surgical article can be removed from the solution where it can be dried at an elevated temperature until the solvent and any residual reactants are removed.

For use in coating applications the aliphatic polyoxaesters should exhibit an inherent viscosity, as measured in a 0.1 gram per deciliter (g/dl) of hexafluoroisopropanol (HFIP), between about 0.05 to about 2.0 dl/g, preferably about 0.10 to about 0.80 dl/g. If the inherent viscosity were less than about 0.05 dl/g, then the polymer may not have the integrity necessary for the preparation of films or coatings for the surfaces of various surgical and medical articles. On the other hand, 15 although it is possible to use polymers with an inherent viscosity greater than about 2.0 dl/g, it may be exceedingly difficult to do so.

Although it is contemplated that numerous surgical articles (including but not limited to endoscopic instruments) can be coated with the polymer of this invention to improve the surface properties of the article, the preferred surgical articles are surgical sutures and needles. The most preferred surgical article is a suture, most preferably attached to a needle. Preferably, the suture is a synthetic absorbable suture. These sutures are derived, for example, from homopolymers and copolymers of lactone monomers such as glycolide, lactide, ε-caprolactone, 1,4-dioxanone, and trimethylene carbonate. The preferred suture is a braided multifilament suture composed of polyglycolide or poly(glycolide-co-lactide).

The amount of coating polymer to be applied on the surface of a braided suture can be readily determined empirically, and will depend on the particular copolymer and suture chosen. Ideally, the amount of coating copolymer applied to the surface of the suture may range from about 0.5 to about 30 percent of the weight of the coated suture, more preferably from about 1.0 to about 20 weight percent, most preferably from 1 to about 5 percent by weight. If the amount of coating on the suture were greater than about 30 weight percent, then it may increase the risk that the coating may flake off when the suture is passed through tissue.

Sutures coated with the polymers of this invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer of this invention.

In another embodiment of the present invention when the article is a surgical needle, the amount of coating applied to the surface of the article is an amount which creates a layer with a thickness ranging preferably between about 2 to about 20 microns on the needle, more preferably about 4 to about 8 microns. If the amount of coating on the needle were such that the thickness of the coating layer was greater than about 20 microns, or if the thickness was less than about 2 microns, then the desired performance of the needle as it is passed through tissue may not be achieved.

In another embodiment of the present invention, the aliphatic polyoxaester can be used as a pharmaceutical carrier in a drug delivery matrix. To form this matrix the polyoxaesters would be mixed with a therapeutic agent to form the matrix. The variety of different therapeutic agents which can be used in conjunction with the aliphatic polyoxaesters of the invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered in any suitable dosage form such as oral, parenteral, a subcutaneously as an implant, vaginally or as a suppository. Matrix formulations containing the aliphatic polyoxaester may be formulated by mixing one or more therapeutic agents with the polyoxaester. The therapeutic agent, may be present as a liquid, a finely divided solid, or any other appropriate physical form. Typically, but optionally, the matrix will include one or more additives, e.g., nontoxic auxiliary substances such as diluents, carriers, excipients, stabilizers or the like. Other suitable additives may be formulated with the polyoxaester and pharmaceutically active agent or compound, however, if water is to be used it should be added immediately before administration.

The amount of therapeutic agent will be dependent upon the particular drug employed and medical condition being treated. Typically, the amount of drug represents about 0.001% to about 70%, more typically about 0.001% to about 50%, most typically about 0.001% to about 20% by weight of the matrix.

The quantity and type of polyoxaester incorporated into the parenteral will vary depending on the release profile desired and the amount of drug employed. The product may contain blends of polyoxaester to provide the desired release profile or consistency to a given formulation.

The polyoxaester, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (over, say 1 to 2,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Individual formulations of drugs and polyoxaester may be tested in appropriate in vitro and in vivo models to achieve the desired drug release profiles. For example, a drug could be formulated with a polyoxaester and orally administered to an animal. The drug release profile could then be monitored by appropriate means such as, by taking blood samples at specific times and assaying the samples for drug concentration. Following this or similar procedures, those skilled in the art will be able to formulate a variety of formulations.

The Examples set forth below are for illustration purposes only, and are not intended to limit the scope of the claimed invention in any way. Numerous additional embodiments within the scope and spirit of the invention will become readily apparent to those skilled in the art.

EXAMPLE 1

Preparation of 3,6-Dioxaoctanedioic acid dimethylester

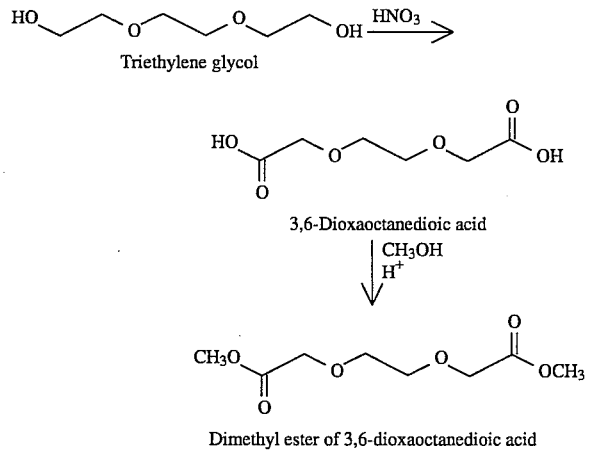

The diacid, 3,6-dioxaoctanedioic acid, was synthesized by oxidation of triethylene glycol. The oxidation was carried out in a 500 milliliter, three-neck round bottom flask equipped with a thermometer, an additional funnel, a gas absorption tube and a magnetic spinbar. The reaction flask was lowered into an oil bath resting upon a magnetic stirrer. To the reaction flask was added 157.3 ml of a 60% nitric acid solution; 37.0 g of triethylene glycol was added to the additional funnel. The contents of the flask were heated to 78°–80° C. A test tube containing 0.5 g of glycol and one milliliter of concentrated nitric acid was warmed in a water bath until brown fumes started appearing. The contents were then added to the reaction flask. The mixture was stirred for a few minutes; the glycol was then carefully added. The rate of addition had to be monitored extremely carefully to keep the reaction under control. The addition rate was slow enough so that the temperature of the exothermic reaction mixture was maintained at 78°–82° C. After the addition was completed (80 minutes), the temperature of the reaction mixture was maintained at 78°–80° C. for an additional hour. While continuing to maintain this temperature range, the excess nitric acid and water was then distilled off under reduced pressure (water suction). The syrupy residue was cooled; some solids appeared. The reaction product had the IR and NMR spectra expected for the dicarboxylic acid; the crude product was used as such for esterification.

Esterification of the crude 3,6-dioxaoctanedioic acid was accomplished as follows: To the reaction flask containing 36 g of the crude diacid, was added 110 ml of methanol. This was stirred for 3 days at room temperature after which 15 g of sodium bicarbonate was added and stirred overnight. The mixture was filtered to remove solids. To the liquor was added an additional 10 g of sodium bicarbonate; this mixture was stirred overnight. The mixture was again filtered; the liquor was fractionally distilled.

NMR analysis of the esterified product showed a mixture of dimethyl triglycolate (78.4 mole %) and monomethyltriglycolate (21.6 mole %). No significant condensation of diacid was observed.

EXAMPLE 2

Preparation of polyoxaester from the methyl esters of 3,6-dioxaoctanedioic acid and ethylene glycol solution of 0.33 M stannous octoate in toluene. After purging the reactor and venting with nitrogen, the temperature was gradually raised over the course of 26 hours to 180° C. A temperature of 180° C. was then maintained for another 20 hours; all during these heating periods under nitrogen at one atmosphere, the methanol formed was collected. The reaction flask was allowed to cool to room temperature; it was then slowly heated under reduced pressure (0.015–1.0 mm) over the course of about 32 hours to 160° C., during which time additional distillates were collected. A temperature of 160° C. was maintained for 4 hours after which a sample, a few grams in size, of the polymer formed was taken. The sample was found to have an inherent viscosity (I.V.) of 0.28 dl/g, as determined in hexaflouroisopropanol (HFIP) at 25° C. at a concentration of 0.1 g/dl. The polymerization was continued under reduced pressure while raising the temperature, in the course of about 16 hours, from 160° C. to 180° C.; a temperature of 180° C. was maintained at for an additional 8 hours, at which time a polymer sample was taken and found to have an I.V. of 0.34 dl/g. The reaction was continued under reduced pressure for another 8 hours at 180° C. The resulting polymer has an inherent viscosity of 0.40 dl/g, as determined in HFIP at 25° C. and at a concentration of 0.1 g/dl.

EXAMPLE 3

Preparation of polyoxaester with 3,6,9-trioxaundecanedioic acid and ethylene glycol A flame dried, mechanically stirred, 250-milliliter glass reactor, suitable for polycondensation reaction, was charged

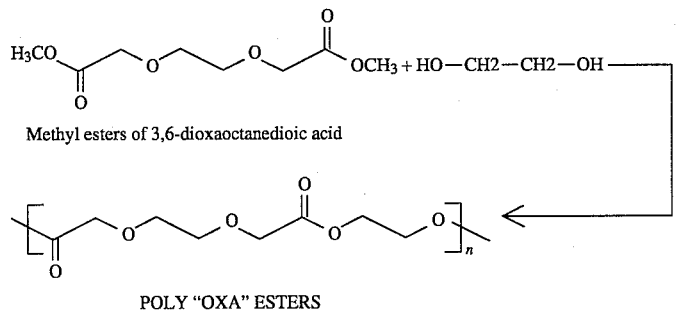

Methyl esters of 3,6-dioxaoctanedioic acid

POLY "OXA" ESTERS

A flame dried, mechanically stirred, 50-milliliter glass reactor suitable for polycondensation reaction, was charged with 20.62 g (approximately 0.1 mole) of the methyl esters of 3,6-dioxaoctanedioic acid from Example 1, 18.62 g (0.3 mole) of distilled ethylene glycol, and 0.0606 ml of a with 44.44 g (0.2 mole) of 3,6,9-trioxaundecanedioic acid, 62.07 g (1.0 mole) of distilled ethylene glycol, and 9.96 milligrams of dibutyltin oxide. After purging the reactor and venting with nitrogen, the contents of the reaction flask were gradually heated under nitrogen at one atmosphere, in the course of about 32

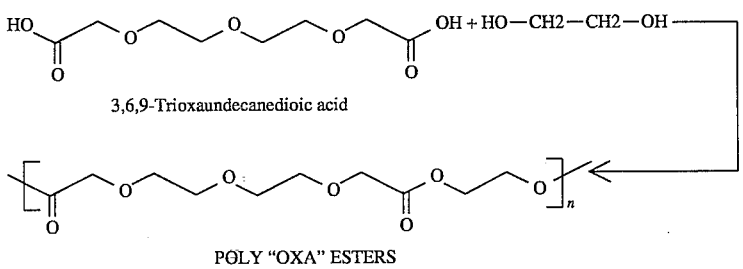

3,6,9-Trioxaundecanedioic acid

POLY "OXA" ESTERS hours, to 180° C., during which time the water formed was collected. The reaction mass was allowed to cool to room temperature. The reaction mass was then heated under reduced pressure (0,015–1.0 mm), gradually increasing the temperature to 180° C. in about 40 hours; during this time additional distillates were collected. The polymerization lo was continued under reduced pressure while maintaining 180° C. for an additional 16 hours. The resulting polymer has an inherent viscosity of 0.63 dl/g as determined in HFIP at 25° C. and at a concentration of 0.1 g/dl.

Example 4

Preparation of polyoxaester with polyglycol diacid and ethylene glycol

A flame dried, mechanically stirred, 500-milliliter

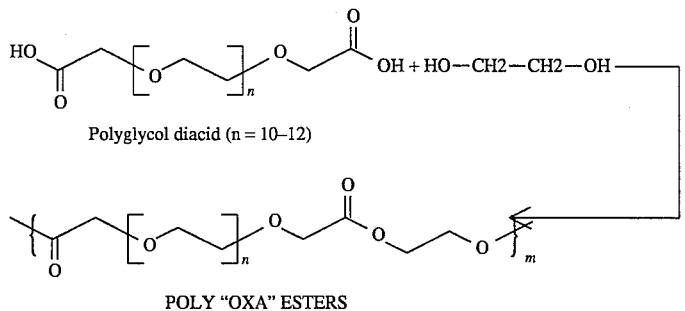

Polyglycol diacid (n = 10–12)

POLY "OXA" ESTERS glass reactor (suitable for polycondensation reaction) was charged with 123.8 g (0.2 mole) polyglycol diacid (molecular weight about 619), 62.07 g (1.0 mole) of distilled ethylene glycol, and 9.96 milligrams of dibutyltin oxide. After purging the reactor and venting with nitrogen, the contents of the reaction flask was heated under nitrogen at one atmosphere, gradually increasing the temperature to 200° C. in about 32 hours; during this time the water formed was collected. The reaction flask was heated gradually under reduced pressure (0,015–1.0 mm) from room temperature to 140° C. in about 24 hours, during which time additional distillates were collected. A polymer sample of about ten grams was taken at this stage, and found to have an I.V. of 0.14 dl/g in HFIP at 25° C., 0.1 g/dl. The polymerization was continued under reduced pressure while heating from 140° C. to 180° C. in about 8 hours, and then maintained at 180° C. for an additional 8 hours. A polymer sample was again taken and found to have an I.V. of 0.17 dl/g. The reaction temperature was then increased to 190° C. and maintained there under reduced pressure for an additional 8 hours. The resulting polymer has an inherent viscosity of 0.70 dl/g as determined in HFIP at 25° C. and at a concentration of 0.1 g/dl.

Example 5

Copolymer of polyoxaester/caprolactone/trimethylene carbonate at 5/5/5 by weight A flame dried, 50-milliliter, round bottom single-neck flask was charged with 5 grams of the aliquot of the polyoxaester of Example 4 having an I.V. of 0.14 dl/g, 5.0 grams (0.0438 mole) of ε-caprolactone, 5.0 grams (0.0490 mole) of trimethylene carbonate, and 0.0094 milliliters of a 0.33 molar solution of stannous octoate in toluene.

The flask was fitted with a magnetic stirrer bar. The reactor was purged with nitrogen three times before venting with nitrogen. The reaction mixture was heated to 160° C. and maintained at this temperature for about 6 hours. The copolymer was dried under vacuum (0.1 mm Hg) at 80° C. for about 16 hours to remove any unreacted monomer. The copolymer has an inherent viscosity of 0.34 dl/g, as determined in HFIP at 25° C. and at a concentration of 0.1 g/dl. The copolymer is a viscous liquid at room temperature. The mole ratio of polyoxaester/PCL/PTMC was found by NMR analysis to be 47.83/23.73/28.45.

Example 6

Copolymer of polyoxaester/caprolactone/glycolide at 6/8.1/0.9 by weight

A flame dried, 25-milliliter, round bottom, singleneck flask was charged with 6 grams of the polyoxaester of Example 4 having an I.V. of 0.17 dl/g., 8.1 grams (0.0731 mole) of ε-caprolactone, 0.9 grams (0.008) mole of glycolide and 0.0080 milliliters of a 0.33 molar stannous octoate solution in toluene. The flask was fitted with a magnetic stirrer bar. The reactor was purged with nitrogen three times before venting with nitrogen. The reaction mixture was heated to 160° C. and maintained at this temperature for about 18 hours. The copolymer has an inherent viscosity of 0.26 dl/g in HFIP at 25° C. and at a concentration of 0.1 g/dl. The copolymer is solid at room temperature. The mole ratio of polyoxaester/PCL/PGA/caprolactone was found by NMR analysis to be 56.54/37.73/3.79/1.94.

Example 7

In Vitro Hydrolysis

The polyoxaester of Example 3 was tested for in vitro hydrolysis at both 50° C. and at reflux temperature. A 100 mg sample of the polyoxaester, placed in 100 ml of a phosphate buffer solution (0.2 M in phosphate, pH 7.27), was completely hydrolyzed in about 7 days at 50° C., whereas at reflux it was completely hydrolyzed in about 16 hours.

Example 8

In Vitro Hydrolysis

Polyoxaester of Example 2 was tested for in vitro hydrolysis at 50° C. and at reflux temperature. A 100 mg sample of the polyoxaester, placed in a 100 ml buffer solution (pH 7.27), was completely hydrolyzed in about 5 days at 50° C., whereas at reflux it was completely hydrolyzed in about 16 hours.

We claim:

1. An aliphatic polyoxaesters comprising a first divalent repeating unit of formula I:

$$[O-C(O)-C(R_1)(R_2)-O-(R_3)-O-C(R_1)(R_2)-C(O)-] \quad I$$

and a second repeating unit selected from the group of formulas consisting of:

$$[-O-R_4-]_A, \quad II$$

$$[-O-R_5-C(O)-]_B, \text{ and} \quad III$$

$$([-O-R_5-C(O)]_P-O-)_L G \quad XI$$

and combinations thereof, wherein $R_1$ and $R_2$ are independently hydrogen or an alkyl group containing 1 to 8 carbon atoms; $R_3$ is an alkylene unit or is an oxyalkylene group of the following formula:

$$-[(CH_2)_C-O-]_D-(CH_2)_B- \quad IV$$

wherein C is an integer in the range of from 2 to about 5, D is an integer in the range of from about 0 to about 12, and E is an integer in the range of from about 2 to about 5, except when D is zero, in which case E will be from 2 to 12; $R_4$ is an alkylene unit containing from 2 to 8 carbon atoms; A is an integer in the range of from 1 to 1,000; $R_5$ is selected from the group consisting of $-C(R_6)(R_7)-$, $-(CH_2)_3-O-$, $-CH_2-CH_2-O-CH_2-$, $-CR_8H-CH_2-$, $-(CH_2)_4-$, $-(CH_2)_F-O-C(O)-$ and $-(CH_2)_F-C(O)-CH_2-$; $R_6$ and $R_7$ are independently hydrogen or an alkyl containing from 1 to 8 carbon atoms; $R_8$ is hydrogen or methyl; F is an integer in the range of from 2 to 6; B is an integer in the range of from 1 to n such that the molecular weight of formula III is less than about 40,000; P is an integer in the range of from 1 to m much that the molecular weight of formula XI is less than about 40,000; G represents the residue minus from 1 to L hydrogen atoms from the hydroxyl groups of an alcohol previously containing from 2 to 12 hydroxyl groups; and L is an integer from about 1 to about 12.

2. The aliphatic polyoxaesters of claim 1 wherein the polymer has the formula:

$$[-O-C(O)-C(R_1)(R_2)-O-(R_3)-O-C(R_1)(R_2)-C(O)-(O-R_4)_A-]_N$$

wherein N is an integer in the range of from about 1 to about 300,000.

3. The aliphatic polyoxaesters of claim 1 wherein the polymer has the formula:

$$[(-C(O)-C(R_1)(R_2)-O-R_3-O-C(R_1)(R_2)-C(O)-(O-R_4)_A-O)_S(C(O)-R_5-O)_B]_W$$

wherein S and W are independently integers in the range of from about 1 to about 1,000.

4. The aliphatic polyoxaesters of claim 1 wherein the polymer has the formula:

$$[(-C(O)-C(R_1)(R_2)-O-R_3-O-C(R_1)(R_2)-C(O)-(O-R_4)_A-O)_x([-O-R_5-C(O)]_P-O-)_L G]_W$$

wherein S and W are independently integers in the range of from about 1 to about 1,000.

5. A device made from analiphatic polyoxaesters comprising a first divalent repeating unit of formula I:

$$[O-C(O)-C(R_1)(R_2)-O-C(R_1)(R_2)-C(O)-] \quad I$$

and a second repeating unit selected from the group of formulas consisting of:

$$[-O-R_4-]_A, \quad II$$

$$[-O-R_5-C(O)-]_B, \text{ and} \quad III$$

$$([-O-R_5-C(O)]_P-O-)_L G \quad XI$$

and combinations thereof, wherein $R_1$ and $R_2$ are independently hydrogen or an alkhyl group containing 1 to 8 carbon atoms; $R_3$ is an alkylene unit or is an oxyalkylene group of the following formula:

$$-[(CH_2)_C-O-]_D-(CH_2)_B-+tm \quad IV$$

wherein C is an integer in the range of from 2 to about 5, D is an integer in the range of from about 0 to abour 12, and E is an integer in the range of from about 2 to about 5, except when D is zero, in which case E will be from 2 to 12; $R_4$ is an alkylene unit containing from 2 to 8 carbon atoms; A is an integer in the range of from 1 to 1,000; $R_5$ is selected from the group consisting of $-C(R_6)(R_7)-$, $-(CH_2)_3-O-$, $-CH_2-CH_2-O-CH_2-$, $-CR_8H-CH_2-$, $-(CH_2)_4-$, $-(CH_2)_F-O-C(O)-$ and $-(CH_2)_F-C(O)-CH_2-$; $R_6$ and $R_7$ are independently hydrogen or an alkyl containing from 1 to 8 carbon atoms; $R_8$ is hydrogen or methyl; F is an integer in the range of from 2 to 6; B is an integer in the range of from 1 to n such that the molecular weight of formula III is less than about 40,000; P is an integer in the range of from 1 to m such that the molecular weight of formula XI is less than about 40,000; G represents the residue minus from 1 to L hydrogen atoms from the hydroxyl groups of an alcohol previously containing from 2 to 12 hydroxyl groups; and L is an integer from about 1 to about 12.

6. The device of claim 5 wherein the device is an absorbable surgical device.

7. The absorbable surgical device of claim 6 wherein the absorbable surgical device is selected from the group consisting of burn dressings, hernia patches, medicated dressings, fascial substitutes, gauze, fabrics, sheets, felts, sponges, gauze bandages, arterial graft, bandages for skin surfaces, suture knot clip, pins, clamps, screws, plates, clips, staples, hooks, buttons, snaps, bone substitutes, intrauterine devices, tubes, surgical instruments, vascular implants, vascular supports, vertebral discs, and artificial skin.

8. The absorbable surgical device of claim 6 wherein the device is a filament.

9. The filament of claim 8 wherein the filament is attached to a needle.

10. A device coated with an absorbable coating comprising an aliphatic polyoxaesters having a first divalent repeating unit of formula I:

$$[O-C(O)-C(R_1)(R_2)-O-(R_3)-O-C(R_1)(R_2)-C(O)-] \quad I$$

and a second repeating unit selected from the group of formulas consisting of:

$$[-O-R_4-]_A, \quad II$$

$$[-O-R_5-C(O)-]_B, \text{ and} \quad III$$

$$([-O-R_5-C(O)]_P-O-)_L G \quad XI$$

and combinations thereof, wherein $R_1$ and $R_2$ are independently hydrogen or an alkyl group containing 1 to 8 carbon atoms; $R_3$ is an alkylene unit or is an oxyalkylene group of the following formula:

$$-[(CH_2)_C-O-]_D-(CH_2)_E- \quad IV$$

wherein C is an integer in the range of from 2 to about 5, D is an integer in the range of from about 0 to about 12) and E is an integer in the range of from about 2 to about 5, except when D is zero, in which case E will be from 2 to 12; $R_4$ is an alkylene unit containing from 2 to 8 carbon atoms; A is an integer in the range of from 1 to 1,000; $R_5$ is selected from the group consisting of $-C(R_6)(R_7)-$, $-(CH_2)_3-O-$, $-CH_2-CH_2-O-CH_2-$, $-CR_8H-CH_2-$, $-(CH_2)_4-$, $-(CH_2)_F-O-C(O)-$ and $-(CH_2)_F-C(O)-CH_2-$; $R_6$ and $R_7$ are independently hydrogen or an alkyl containing from 1 to 8 carbon atoms; $R_8$ is hydrogen or methyl; F is an integer in the range of from 2 to 6; B is an integer in the range of from 1 to n such that the molecular weight of formula III is less than about 40,000; P is an integer in the range of from 1 to m such that the molecular weight of formula XI is less than about 40,000; G represents the residue minus from 1 to L hydrogen atoms from the hydroxyl groups of an alcohol previously containing from 2 to 12 hydroxyl groups; and L is an integer from about 1 to about 12 wherrein the inherent viscosity of the polyoxaester is in the range of from about 0.05 to about 2.0 deciliters per gram (dl/g) as measured in a 0.1 g/dl solution of hexafluoroisopropanol (HFIP) at 25° C.

11. The device of claim 10 wherein the device is a suture.

12. The device of claim 11 wherein the suture is attached to a needle.

13. A device coated with an absorbable coating comprising an aliphatic polyoxaesters having a first divalent repeating unit of formula I:

$$[O-C(O)-C(R_1)(R_2)-O-(R_3)-O-C(R_1)(R_2)-C(O)-] \quad I$$

and a second repeating unit selected from the group of formulas consisting of:

$$[-O-R_4-]_A, \quad II$$

$$[-O-R_5-C(O)-]_B, \text{ and} \quad III$$

$$([-O-R_5-C(O)]_P-O-)_L G \quad XI$$

and combinations thereof, wherein $R_1$ and $R_2$ are independently hydrogen or an alkyl group containing 1 to 8 carbon atoms; $R_3$ is an alkylene unit [containing from 2 to 12 carbon atoms] or is an oxyalkylene group of the following formula:

$$-[(CH_2)_C-O-]_D-(CH_2)_E- \quad IV$$

wherein C is an integer in the range of from 2 to about 5, D is an integer in the range of from about 0 to about 12, and E is an integer in the range of from about 2 to about 5, except when D is zero, in which case E will be from 2 to 12; $R_4$ is an alkylene unit containing from 2 to 8 carbon atoms; A is an integer in the range of from 1 to 1,000; $R_5$ is selected from the group consisting of $-C(R_6)(R_7)-$, $-(CH_2)_3-O-$, $-CH_2-CH_2-O-$ $CH_2-$, $-CR_8H-CH_2-$, $-(CH_2)_4-$, $-(CH_2)_F-O-C(O)-$ and $-(CH_2)_F-C(O)-CH_2-$; $R_6$ and $R_7$ are independently hydrogen or an alkyl containing from 1 to 8 carbon atoms; $R_8$ is hydrogen or methyl; F is an integer in the range of from 2 to 6; B is an integer in the range of from 1 to n such that the molecular weight of formula III is less than about 40,000; P is an integer in the range of from 1 to m such that the molecular weight of formula XI is less than about 40,000; G represents the residue minus from 1 to L hydrogen atoms from the hydroxyl groups of an alcohol previously containing from 2 to 12 hydroxyl groups; and L is an integer from about 1 to about 12 wherein the inherent viscosity of the polyoxaester is in the range of from about 0.05 to about 2.0 deciliters per gram (dl/g) as measured in a 0.1 g/dl solution of hexafluoroisopropanol (HFIP) at 25° C.

14. The device of claim 5 wherein the aliphatic polyoxaesters have the formula:

$$[-O-C(O)-C(R_1)(R_2)-O-(R_3)-O-C(R_1)(R_2)-C(O)-O-R_4)_A-]_N$$

wherein N is an integer in the range of from about 1 to about 300,000.

15. The device of claim 5 wherein the aliphatic polyoxaesters have the formula:

$$[(-C(O)-C(R_1)(R_2)-O-R_3-O-C(R_1)(R_2)-C(O)-(O-R_4)_A-O)_S (C(O)-R_5-O)_B]_W$$

wherein S and W are independently integers in the range of from about 1 to about 1,000.

16. The device of claim 5 wherein the aliphatic polyoxaesters have $$[(-C(O)-C(R_1)(R_2)-O-(R_3)-O-C(R_1)(R_2)-C(O)-(O-R_4)_A-O)_S ([-O-R_5-C(O)]_P-O-)_L G]_W$$

wherein S and W are independently integers in the range of from about 1 to about 1,000.

17. The device coated with an absorbable coating of claim 10 wherein the aliphatic polyoxaesters have the formula:

$$[-O-C(O)-C(R_1)(R_2)-O-(R_3)-O-C(R_1)(R_2)-C(O)-(O-R_4)_A-]_N$$

wherein N is an integer in the range of from about 1 to about 300,000.

18. The device coated with an absorbable coating of claim 10 wherein the aliphatic polyoxaesters have the formula:

$$[(-C(O)-C(R_1)(R_2)-O-R_3-O-C(R_1)(R_2)-C(O)-(O-R_4)_A-O)_S (C(O)-R_5-O)_B]_W$$

wherein S and W are independently integers in the range of from about 1 to about 1,000.

19. The device coated with an absorbable coating of claim 10 wherein the aliphatic polyoxaesters have the formula:

$$[(-C(O)-C(R_1)(R_2)-O-R_3-O-C(R_1)(R_2)-C(O)-(O-R_4)_A-O)_S ([-O-R_5-C(O)]_P-O-)_L G]_W$$

wherein S and W are independently integers in the range of from about 1 to about 1,000.

20. The drug delivery matrix of claim 13 wherein the aliphatic polyoxaester has the formula:

$$[-O-C(O)-C(R_1)(R_2)-O-(R_3)-O-C(R_1)(R_2)-C(O)-(O-R_4)_A-]_N$$

wherein N is an integer in the range of from about 1 to about 300,000.

21. The drug delivery matrix of claim 13 wherein the aliphatic polyoxaester has the formula:

$$[(-C(O)-C(R_1)(R_2)-O-R_3-O-C(R_1)(R_2)-C(O)-(O-R_4)_A-O)_S (C(O)-R_5-O)_B]_W$$

wherein S and W are independently integers in the range of from about 1 to about 1,000.
22. The drug delivery matrix of claim 13 wherein the aliphatic polyoxaester has the formula:
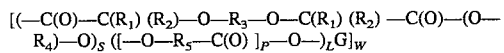
wherein S and W are independently integers in the range of from about 1 to about 1,000.
* * * * *

UNITED STATES PATENT AND TRADEMARK OFFICE
CERTIFICATE OF CORRECTION

PATENT NO. : 5,464,929
DATED : November 7, 1995
INVENTOR(S) : Rao S. Bezwada et al It is certified that error appears in the above-indentified patent and that said Letters Patent is hereby corrected as shown below:

Column 13,
Claim 1, line 29, formula should be:

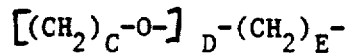

Col. 14,
Claim 5, line 6, "analiphatic" should be -- an aliphatic --.

Claim 5, line 9, formula should be:

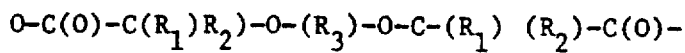

Claim 5, line 18, "alkhyl" should be "alkyl".
Claim 5, line 21, formula should read:

Col. 15, 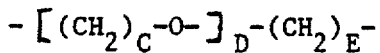

Claim 10, line 8, formula should read:

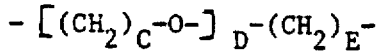

Claim 10, line 10, "12)" should be --12, --.

Claim 10, line 28, "wherrein" should be -- wherein --.

Claim 13, line 49, "containing from 2 to 12 carbon atoms" should be deleted.

UNITED STATES PATENT AND TRADEMARK OFFICE
CERTIFICATE OF CORRECTION

PATENT NO. : 5,464,929
DATED : November 7, 1995
INVENTOR(S) : Rao S. Bezwada et al It is certified that error appears in the above-indentified patent and that said Letters Patent is hereby corrected as shown below:

Claim 13, line 54, formula should read:

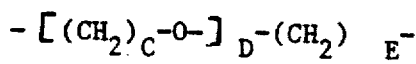

Claim 13, line 63, "$-(CH_2)_P-$" should read -- $-(CH_2)_F-$ --

Claim 16, line 28, formula should read:

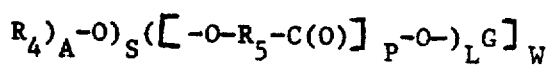

Signed and Sealed this

Fourth Day of November, 1997

BRUCE LEHMAN

*Attest:*

*Attesting Officer*   Commissioner of Patents and Trademarks